(12) United States Patent
Homsma et al.

(10) Patent No.: US 11,339,290 B2
(45) Date of Patent: May 24, 2022

(54) KIT OF PARTS FOR PREPARING A BIOCOMPATIBLE POLYMER

(71) Applicant: TRIPLEMED B.V., Geleen (NL)

(72) Inventors: Tjeerd Homsma, Geleen (NL); Martinus Cornelis Van Osch, Geleen (NL)

(73) Assignee: TRIPLEMED B.V., Geleen (NL)

( * ) Notice: Subject to any disclaimer, the term of this patent is extended or adjusted under 35 U.S.C. 154(b) by 0 days.

(21) Appl. No.: 17/599,858

(22) PCT Filed: Apr. 3, 2020

(86) PCT No.: PCT/EP2020/059576
§ 371 (c)(1),
(2) Date: Sep. 29, 2021

(87) PCT Pub. No.: WO2020/201514
PCT Pub. Date: Oct. 8, 2020

(65) Prior Publication Data
US 2022/0098411 A1  Mar. 31, 2022

(30) Foreign Application Priority Data
Apr. 4, 2019 (EP) .................................. 19167326

(51) Int. Cl.
*C08L 83/04* (2006.01)
*A61L 24/04* (2006.01)

(52) U.S. Cl.
CPC ............. *C08L 83/04* (2013.01); *A61L 24/043* (2013.01); *A61L 2430/36* (2013.01)

(58) Field of Classification Search
None
See application file for complete search history.

(56) References Cited

U.S. PATENT DOCUMENTS

| | | | | |
|---|---|---|---|---|
| 4,401,491 A * | 8/1983 | Modic | ...................... | A62C 3/16 156/48 |
| 5,106,939 A * | 4/1992 | Sumpter | .............. | C08K 5/0091 528/15 |
| 5,132,385 A * | 7/1992 | Sumpter | ................. | C08L 83/04 528/15 |
| 5,132,442 A * | 7/1992 | Sumpter | .............. | C08K 5/0091 556/136 |
| 5,580,921 A * | 12/1996 | Stepp | ........................ | A61K 6/90 524/731 |
| 5,718,586 A * | 2/1998 | Sharp | ...................... | C08L 83/04 428/447 |
| 6,313,190 B1 * | 11/2001 | Bublewitz | ............... | C08L 83/04 523/109 |
| 6,555,056 B2 * | 4/2003 | Nakagawa | ............... | C08J 3/241 422/1 |
| 7,335,708 B2 * | 2/2008 | Bublewitz | ............... | C08L 83/04 523/115 |
| 2008/0226572 A1* | 9/2008 | Cassin | ................... | A61K 8/895 424/61 |
| 2010/0152135 A1* | 6/2010 | Blin | ........................ | A61K 8/922 514/63 |
| 2018/0186938 A1* | 7/2018 | Ou | ....................... | A61M 5/2448 |
| 2018/0369446 A1* | 12/2018 | de Vries | .............. | A61L 24/0089 |

FOREIGN PATENT DOCUMENTS

| | | |
|---|---|---|
| EP | 1435249 A1 | 7/2007 |
| NL | 2015807 B1 | 6/2017 |
| WO | 9508289 A2 | 3/1995 |
| WO | 2018081837 A2 | 5/2018 |

OTHER PUBLICATIONS

Japanese Office Action dated Mar. 8, 2022 for family member Application No. 2021-560485.

* cited by examiner

*Primary Examiner* — Peter A Salamon
(74) *Attorney, Agent, or Firm* — Hudak, Shunk & Farine Co. LPA

(57) ABSTRACT

A kit of parts suitable for preparing a cured biocompatible polymer material, the kit including at least 2 containers each containing a fluid component, which components—when mixed—form a fluid curable biocompatible polymer composition, which upon curing forms the cured biocompatible silicone polymer material.

20 Claims, No Drawings

KIT OF PARTS FOR PREPARING A BIOCOMPATIBLE POLYMER

FIELD OF THE INVENTION

The invention relates to a kit of parts for preparing a cured biocompatible polymer material, a curable biocompatible composition obtained by mixing the components of the kit of parts and a cured biocompatible polymer composition suitable for in vivo use in a medical treatment, in particular in the treatment of a subject having an aneurysm.

BACKGROUND OF THE INVENTION

Treatments of aneurysms with curable polymer compositions have been a topic of research and development for several decades. Aneurysms are local dilatations in blood vessels, in particular arteries that gradually enlarge in time. Unless an aneurysm is adequately treated, it may eventually rupture and cause severe damage to the body, possibly even result in shock or death. Aortic aneurysms are in particular an important cause of death in human adults of 55 years and older.

Traditional repair of an aneurysm entails a major operation with an incision into the aneurysm, evacuation of the clot that is usually contained within, placement of a synthetic graft and wrapping of the graft with the remnants of the artery wall.

A more recent development is the endovascular stent technique, that has become a common technique to treat abdominal aortic aneurysms. This procedure does not require general anaesthesia and can be done less invasively by simply placing a self-expanding stent via a catheter passed through one of the femoral arteries into the aneurysm to stabilise it. Less fit patients are able to withstand the procedure, hospital stay is cut to 1 to 2 days, and post-operative recovery is shortened considerably.

In WO 95/08289 it is proposed to repair cardiovascular anomalies via the introduction of a photo-activatable biopolymer, which is introduced to the anomaly via a catheter system, after which the polymer is cross-linked. The publication mentions several examples of potentially suitable polymers, wherein it is suggested to be advantageous that the polymers are not only photo-activatable but also biodegradable and resorbable.

A catheter system for delivering fluid materials, such as medicaments to a body vessel is reported in EP-A 0 667 131. The fluid material is for example a mixture comprising an epoxy resin that cures in the presence of ions.

EP-A 1 435 249 and NL 2015807 relate to biocompatible polymer composition for use in the treatment of in vivo vessel repair, such as the repair of an aortic aneurysm, with satisfactory properties with respect to—amongst others— curing behaviour, low toxicity, biocompatibility and durability in vivo.

US2018/0369446 describes a kit of parts comprising tantalum for improved visibility of a silicon polymer composition which is used for repair of an aneurysm.

The biocompatible polymer compositions known in the art have a disadvantage of either having a rather high viscosity, which limits the ability to inject the compositions through thin catheters, or a low viscosity in order to inject the polymer thru thin catheters (eg for treatment of aneurysms in the brain) but then the material is prone to embolize and cure in very distal locations resulting in ischemia of blood vessels that are not targeted. Alternatively, when the viscosity is reduced, the polymerization may be too slow, whereby leakage of uncured polymer composition can occur within the human body resulting in failure of the aneurysm repair or other complications during the surgery.

Alternatively, solutions like glue (adhesives) have the disadvantage that no good filling of the aneurysm sac or endoleak is achieved and curing is very fast and uncontrolled. The present invention intends to solve at least one or more of the above problems.

SUMMARY OF THE INVENTION

The invention relates to a kit of parts suitable for preparing a cured biocompatible polymer material, the kit comprising at least 2 containers each containing a fluid component, which components—when mixed—form a fluid curable biocompatible polymer composition, which upon curing forms the cured biocompatible silicone polymer material, wherein a first container comprises a fluid component A, which component A comprises a) A divinyl substituted polydimethylsiloxane A1 having a viscosity between 50 and 600 cSt at 25° C.,
b) Optionally a divinyl substituted polydimethylsiloxane A2 having a viscosity between 1000 and 20000 cSt at 25° C.,
c) A Pt catalyst soluble in Polydimethylsiloxane (PDMS)
d) Optionally a hydrophobic fumed silica $FS_A$ having been partially surface treated
e) Optionally a crosslinker A3 having more than 2 vinyl groups per molecule and wherein a second container comprises a fluid component B, which component B comprises,
f) Optionally a dihydride substituted polydimethylsiloxane B1 having a viscosity between 50 and 600 cSt,
g) Optionally a dihydride substituted polydimethylsiloxane B2 having a viscosity between 1000 and 20000 cSt at 25° C.,
h) Optionally a hydrophobic fumed silica $FS_B$ having been partially surface treated
i) a crosslinker B3 having more than 2 hydrosilyl groups,
wherein the amount of polydimethylsiloxane A1 is at least 70 wt % relative to the total of polydimethylsiloxane A1 and polydimethylsiloxane A2,
wherein (if B1 and B2 are present) the amount of polydimethylsiloxane B1 is at least 70 wt % relative to the total of polydimethylsiloxane B1 and polydimethylsiloxane B2,
wherein the amount of crosslinker A3 ranges between 0 and 10 wt % relative to the weight of component A,
wherein the amount of $FS_A$ and $FS_B$ ranges between 2 and 30 wt % relative to the total weight of component A+component B and wherein components A and B when mixed form a composition having a viscosity of at least 10 Pa·s when sheared at $1\ s^{-1}$, and a viscosity below 2.7 Pa·s when sheared at $600\ s^{-1}$ and wherein the viscosity of the composition recovers to a value of at least 10 Pa·s when high shearing is stopped with a recovery time of less than 60 sec, wherein the viscosity is determined with a Haake VTiQAir rheometer at 37° C. temperature.

The kit of parts contains 2 components A and B which form a curable biocompatible composition which has a high viscosity in the absence of shear, which has a low viscosity in the presence of shear, which gives an easy dosage through thin needles, and the composition gives a quick recovery of the viscosity with high dynamic yield stress after injection, such that a polymer depot can be formed but minimal to no leakage of polymer composition will occur. Furthermore, the kit of parts can be easily sterilised using dry- or moist-heat, as the components are not heat-sensitive.

The cured polymer will show good strength, and elongation while still being elastic with low hardness.

DETAILED DESCRIPTION OF THE INVENTION

The kit of parts has two components A and B, which in use are mixed together to provide a curable biocompatible composition.

The kit of parts can simply be used to prepare the curable fluid polymer composition by mixing the components. This is conveniently achieved using a static mixer, although another type of mixer can be used. The volume to volume ratio of component A:component B is usually in the range of 1:3 to 3:1. Preferably the volume ratio (at 20° C.) of component A to component B ranges between 1:2 and 2:1, more preferably between 1:1.5 and 1.5:1, such that mixing of components A and B is easy in practice. The volume ratio can be outside these preferred ranges, but this is not preferred in view of ease of use.

The components A and B are both fluids, having a viscosity preferably between 10 and 200 Pa·s at a shear rate of 1 $s^{-1}$, and preferably a viscosity below 2.7 Pa·s, more preferably a viscosity below 2 Pa·s at a shear rate of 600 $s^{-1}$.

The containers for the fluid components preferably are part of a multi-barrel syringe (e.g. double barrel or triple barrel), each barrel containing one of the fluid components. In particular for such kit of parts, it is convenient that about equal volumes of each of the components are present in the kit. Dependent on the intended use, the kit may further comprise one or more additional items, in particular one or more items selected from the group consisting of static mixers, catheters, catheter balloons, stents and endo-grafts. Further, the kit may be provided with instructions for use.

The components A and B are preferably free of components dissolvable in water or blood.

The polymer composition obtained by mixing the components of the kit of parts is curable without the necessity of any component dissolving or diffusing out of said composition. In particular, the components of the kit of parts are preferably free of solvents, like DMSO, that are soluble in water and/or water-soluble buffer components, of which glycylglycine and HEPES are examples.

Before curing the composition is fluid, i.e. it is capable of flowing (usually while being pumped) through a lumen for delivery of the composition into the aneurysm. After curing the composition made by mixing component A and component B a solid material is obtained.

Component A

The first container comprises a fluid component A, which component A comprises a) A divinyl substituted polydimethylsiloxane A1 (PDMS A1) having a viscosity between 50 and 600 cSt at 25° C., b) Optionally a divinyl substituted polydimethylsiloxane A2 (PDMS A2) having a viscosity between 1000 and 20000 cSt at 25° C., c) A Pt catalyst soluble in Polydimethylsiloxane, d) Optionally a hydrophobic fumed silica $FS_A$ having been partially surface treated e) Optionally a crosslinker A3 having more than 2 vinyl groups per molecule.

PDMS A1 is a divinyl substituted polydimethylsiloxane A1 having a viscosity between 50 and 600 cSt at 25° C. The viscosity average molecular weight of this divinyl substituted polydimethylsiloxane (PDMS) ranges between 4000 and 20000 Da. PDMS A1 has preferably a viscosity between 0.3 and 1 Pa·s when sheared at 1 $s^{-1}$. PDMS A1 can also be a blend of polymers, for example a first PDMS A1-1 having a viscosity of 100 cSt blended with a second PDMS A1-2 having a viscosity of 500 cSt.

Preferably the two vinyl groups are attached to each terminal of the polymer molecule, such that a polymer molecule starts with a vinyl group, the main chain of the polymer is a linear PDMS and the polymer molecule ends with the second vinyl group.

Component A can contain a higher viscosity divinyl substituted polydimethylsiloxane A2 (PDMS A2), having a viscosity between 1000 and 20000 cSt at 25° C. Preferably this PDMS A2 has also 2 terminal vinyl group, one at each end of the PDMS main chain.

The amount of PDMS A1 is at least 70 wt % relative to the total of PDMS A1 and PDMS A2.

Component A can have a crosslinker A3, which has more than 2 vinyl groups in each molecule. Examples of crosslinkers A3 are functionalised molecular silica compounds, such as Vinyl Q®, P.O.S.S. compounds and 1,3,5,7-tetravinyl-1,3,5,7-tetramethylcyclotetrasiloxane.

The amount of crosslinker A3 ranges between 0 and 10 wt % relative to the weight of component A, preferably between 1 and 5 wt %. Crosslinker A3 can also function as an inhibitor for the Pt-catalyst. This inhibitor (for example 1,3,5,7-tetravinyl-1,3,5,7-tetramethylcyclotetrasiloxane) can stop or retard the reaction of the Pt for a certain amount of time, but may also stabilize the Pt-catalyst for example during and after steam sterilization of component A.

Component A comprises a Pt-catalyst which is soluble in polydimethylsiloxane.

Examples of suitable catalysts are known in the art. One example of a suitable catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220, 972, and Speier's catalyst as disclosed in Speier, J. L, Webster J. A. and Barnes G. H., J. Am. Chem. Soc. 79, 974 (1957).

Preferred examples of suitable Pt catalysts are Pt-vinyl siloxane complexes.

Highly preferred examples of platinum catalysts are platinum complexes, in particular platinum complexes selected from the group consisting of platinum-divinyltetramethyldisiloxane complexes. The concentration of curing catalyst can readily be determined depending upon the composition and the desired curing time. In particular good results have been achieved with a platinum catalyst in a concentration of at least 5 ppm (based upon the total weight of the biocompatible polymer composition). Particular favourable with respect to the curing time has been found to be a concentration of about 5 to 500 ppm.

Component A can comprise a hydrophobic fumed silica $FS_A$ having been partially surface treated. Fumed silica $FS_A$ has a number average particle size typically ranging between 10 and 100 nm, and its surface is partially treated with an organic agent to provide organic groups attached to the surface of the fumed silica. The fumed silica $FS_A$ preferably has 0.5-5 wt % C, which partly covers the surface of the fumed silica.

The amount of fumed silica $FS_A$ preferably ranges between 2 and 30 wt % relative to component A, more preferably between 15-25 wt %. Component A can also contain a mixture of different hydrophobic fumed silicas.

In a preferred embodiment the component A and/or component B also comprise between 0.1 and 5 wt % of a hydrophilic fumed silica. A hydrophilic fumed silica has preferably not been surface treated with organic groups.

The addition of a hydrophilic fumed silica can assist in the rapid recovery of the low shear viscosity after component A or B or the mixture of A+B being sheared to show a low viscosity. Thereby the addition of hydrophilic fumed silica can prevent the leakage of the blend of A+B when used in vivo and thereby prevents complications to a patient.

Component B

The second container comprises a fluid component B, which component B comprises a) Optionally a dihydride substituted polydimethylsiloxane B1 (PDMS B1) having a viscosity between 50 and 600 cSt,
b) Optionally a dihydride substituted polydimethylsiloxane B2 (PDMS B2) having a viscosity between 1000 and 20000 cSt at 25° C.,
c) Optionally a hydrophobic fumed silica $FS_B$ having been partially surface treated
d) a crosslinker B3 having more than 2 hydrosilyl groups.

PDMS B1 is a dihydride substituted polydimethylsiloxane B1 having a viscosity between 50 and 600 cSt at 25° C. The viscosity average molecular weight of this PDMS B1 ranges between 4000 and 20000 Da. PDMS B1 has preferably a viscosity between 0.3 and 1 Pa·s when sheared at 1 $s^{-1}$.

A dihydride substituted PDMS is a polymer having two hydrosilyl (Si—H) groups in the molecule. A hydrosilyl group is a group containing a silicon atom and at least one hydrogen atom bound to the Si atom. The Si—H is also called a silicon hydride.

PDMS B1 can also be a blend of polymers, for example a first PDMS B1-1 having a viscosity of 100 cSt blended with a second PDMS B1-2 having a viscosity of 500 cSt at 25° C.

Preferably the two hydrosilyl groups are attached to each terminal of the PDMS, such that a PDMS molecule starts with a hydrosilyl group, the main chain of the polymer is a linear PDMS and the PDMS molecule ends with a second hydrosilyl group.

Preferably PDMS B1 is present as part of component B.

Component B can contain a higher viscosity dihydride substituted polydimethylsiloxane B2 (PDMS B2), having a viscosity between 1000 and 20000 cSt at 25° C. Preferably this PDMS 82 has also 2 terminal hydrosilyl groups, one at each end of the PDMS main chain.

The amount of PDMS B1 is at least 70 wt % relative to the total of PDMS B1 and PDMS B2. PDMS B2 can be present in addition to PDMS B1. It is not preferred that PDMS B2 is present, in the absence of PDMS B1 in component B.

Component B comprises a crosslinker B3, having more than 2 hydrosilyl groups.

In one embodiment component B contains only a crosslinker B3, but no PDMS B1 or PDMS B2. Preferably however, at least PDMS B1 is present and the amount of crosslinker B3 ranges between 1 and 10 wt % relative to the weight of component B.

Examples of suitable crosslinking agents B3 are polyalkylhydrosiloxane polymers, including fluorinated polyalkylhydrosiloxane polymers. Very good results, in particular in combination with a silicon (pre-)polymer have been achieved with a polyalkylhydrosiloxane polymer.

A preferred polyalkylhydrosiloxane polymer as a crosslinker B3 is a copolymer of alkylhydrosiloxane moieties and dialkylsiloxane moieties, preferably of methylhydrosiloxane moieties and dimethylsiloxane moieties.

Preferably the amount of dialkylsiloxane moieties—in particular dimethylsiloxane moieties—and/or the amount of alkylhydrosiloxane moieties—in particular methylhydrosiloxane moieties—in a polyalkylhydrosiloxane polymer is 1-100, and more preferably 5 to 20. The dialkylsiloxane-alkylhydrosiloxane copolymer may be a random, alternating or 5 block copolymer.

Preferred examples of crosslinking agent B3 are polymethylhydrosilanes, such as for examples HMS301 (having 25-35 mol % Si—H) and HMS082 (having between 7 and 9 mol % Si—H).

The molar ratio of the hydrosilyl groups in the crosslinker B3 to the hydrosilyl groups present in PDMS B1+PDMS B2 preferably ranges between 1:1 and 3:1. Preferably this molar ratio ranges between 1.25:1 and 2.5:1.

The molar ratio of all vinyl groups from PDMS A1+PDMS A2 and (optional) crosslinker A3 of component A to all hydrosilyl groups from PDMS B1+PDMS B2+crosslinker B3 may range between 1:1 and 1:6. It is however preferred that this molar ratio ranges between 1:2 and 1:1. More preferably this range is between 1:1.5 and 1:1.25.

Component B can comprise a hydrophobic fumed silica $FS_B$ having been partially surface treated. Fumed silica $FS_B$ has a number average particle size typically ranging between 10 nm and 100 nm, and its surface is partially treated with an organic agent. The fumed silica $FS_B$ preferably has 0.5-5 wt % C, which partly covers the surface of the fumed silica.

The amount of fumed silica $FS_B$ preferably ranges between 2 and 30 wt % relative to component B, more preferably between 15 and 25 wt %. Component B can also contain a mixture of hydrophobic fumed silicas.

At least one of the components A or B comprises a hydrophobic fumed silica. Preferably both component A and component B comprise a hydrophobic fumed silica.

The amount of $FS_A$ and $FS_B$ ranges between 2 and 30 wt % relative to the total weight of component A+component B. The amount of $FS_A$ and $FS_B$ is the sum of $FS_A$ (in component A) and $FS_B$ (in component B). Preferably the amount of $FS_A$ and $FS_B$ ranges between 4 and 20 wt %, relative to the total weight of component A+B.

$FS_A$ and $FS_B$ can be the same or different.

$FS_A$ and $FS_B$ are surface modified with organic groups. Examples of organic groups are methyl, polydimethylsiloxane, dimethylsilyl, trimethylsilyl, hexamethylsilazane, dimethyldichlorosilane, tetra(dimethylsiloxane), Aminosilane, Alkylsilane and the like.

$FS_A$ and $FS_B$ typically have a BET surface (m2/g) between 10 and 200.

Commercial examples of $FS_A$ and $FS_B$ are Aerosil R8200, RY50 and R972 of Evonik.

In a preferred embodiment of the invention PDMS A1 and PDMS A2 have each one terminal vinyl group at both ends of the polymer chain and PDMS B1 and PDMS B2 have each one terminal Si—H group at both ends of the polymer chain.

In a preferred embodiment, the total amount of PDMS A1+A2, fumed silica $FS_A$ and crosslinker A3 is at least 50 wt % of component A, more preferably at least 80 wt % of component A.

In a preferred embodiment, the total amount of PDMS B1+B2, fumed silica $FS_B$ and crosslinker B3 is at least 50 wt % of component B, more preferably at least 80 wt % of component B.

In a preferred embodiment the amount of solvent in each component A and component B is less than 2 wt % relative to the weight of component A and B.

The presence of $FS_A$ and $FS_B$ makes component A, component B, and the mixture of A+B shear thinning. At low shear (for example 1 s$^{-1}$) a high viscosity is obtained, which reduces the flow of uncured polymer composition in vivo. Upon shear however, the viscosity drops to a level of less than 2.7 Pa·s, more preferably less than 2.0 Pa·s, when sheared at 600 s$^{-1}$.

In addition to the shear thinning effect, it is also important that the viscosity recovers quickly to a value above 10 Pa·s, to prevent embolization of polymer composition.

Therefore the curable biocompatible polymer composition obtained by mixing components A and B form a composition having a viscosity of at least 10 Pa·s when sheared at 1 s$^{-1}$, and a viscosity below 2.7 Pa·s when sheared at 600 s$^{-1}$ and wherein the viscosity of the composition recovers to a value of at least 10 Pa·s when high shearing is stopped with a recovery time of less than 60 sec, preferably less than 10 sec, most preferably less than 5 sec.

The viscosity is determined using a Haake VTiQAir Rheometer using a CC-insert. The samples have been tested with a gap of 0.100 mm and 35 mm 2° cone and plate at 37° C.

In order to arrive at the required high viscosity at low shear it is preferred that at least the high molecular weight component PDMS A2 or PDMS B2 is present in the kit of parts. It is preferred that the amount of PDMS A2+PDMS B2 is between 10 and 30 wt % relative to the amount of PDMS A1+PDMS A2+PDMS B1+PDMS B2.

In one embodiment the component A and/or component B comprise a X-ray contrast agent. Examples of suitable contrast agents metal particles, like for example barium sulphate, bismuth, iodine, tungsten, tantalum, gold, platinum and silver particles.

Preferably the contrast agent is biocompatible. Preferably the contrast agent comprises tantalum.

In a preferred embodiment, the present invention relates to a kit of parts suitable for preparing a cured biocompatible polymer material, the kit comprising at least 2 containers each containing a fluid component, which components—when mixed—form a fluid curable biocompatible polymer composition, which upon curing forms the cured biocompatible silicone polymer material, wherein a first container comprises a fluid component A, which component A comprises a) A divinyl substituted polydimethylsiloxane A1 having a viscosity between 50 and 600 cSt at 25° C., b) Optionally a divinyl substituted polydimethylsiloxane A2 having a viscosity between 1000 and 20000 cSt at 25° C., c) A Pt catalyst soluble in Polydimethylsiloxane (PDMS)

d) a hydrophobic fumed silica $FS_A$ having been partially surface treated e) Optionally a crosslinker A3 having more than 2 vinyl groups per molecule and wherein a second container comprises a fluid component B, which component B comprises, f) a dihydride substituted polydimethylsiloxane B1 having a viscosity between 50 and 600 cSt, g) Optionally a dihydride substituted polydimethylsiloxane B2 having a viscosity between 1000 and 20000 cSt at 25° C., h) a hydrophobic fumed silica $FS_B$ having been partially surface treated i) a crosslinker B3 having more than 2 hydrosilyl groups, wherein the amount of polydimethylsiloxane A1+B1 is between 70-90 wt % relative to the total of polydimethylsiloxane A1+A2+B1+B2, wherein the amount of polydimethylsiloxane B1 is at least 70 wt % relative to the total of polydimethylsiloxane B1 and polydimethylsiloxane B2, wherein the amount of crosslinker A3 ranges between 0 and 10 wt % relative to the weight of component A, wherein the amount of $FS_A$ and $FS_B$ ranges between 2 and 30 wt % relative to the total weight of component A+component B, and wherein components A and B when mixed form a composition having a viscosity of at least 10 Pa·s when sheared at 1 s$^{-1}$, and a viscosity below 2.7 Pa·s when sheared at 600 s$^{-1}$ and wherein the viscosity of the composition recovers to a value of at least 10 Pa·s when high shearing is stopped with a recovery time of less than 60 sec, wherein the viscosity is determined according to with a Haake VTiQAir rheometer at 37° C. temperature.

Preferably at least either PDMS A2 or PDMS B2 is present in the kit of parts, wherein the amount of PDMS A2+PDMS B2 is between 10 and 30 wt % relative to the amount of PDMS A1+PDMS A2+PDMS B1+PDMS B2

The invention also relates to a curable biocompatible composition, obtained by mixing component A and component B. preferably the curable composition has a viscosity of at least 10 Pa·s when sheared at 1 s$^{-1}$, and a viscosity below 2.7 Pa·s when sheared at 600 s$^{-1}$ and wherein the viscosity of the composition recovers to a value of at least 10 Pa·s when high shearing is stopped with a recovery time of less than 60 sec, wherein the viscosity is determined with a Haake VTiQAir rheometer at 37° C.

The curable biocompatible composition can be used for treatment of an aneurysm.

The invention also relates to the a cured biocompatible polymer material obtained by combining components A and B of the kit of parts as defined above to arrive at a curable biocompatible composition which is cured under the influence of the Pt-catalyst.

Preferably the cured composition has a Young modulus of between 0.3 and 3 MPa, preferably between 0.4 and 1 MPa and a hardness between 10 and 44 ShA, preferably between 11 and 25 ShA.

The cured polymer material has a strain or an elongation at break of between 50 and 600%, preferably between 100 and 300%, and a stress at break of between 100 and 1000 kPa, preferable between 200 and 500 kPa.

The invention further relates to a curable silicone polymer composition, obtainable by a method according to the invention.

The invention further relates to a method for preparing a cured biocompatible silicone polymer material including an X-ray contrast agent, comprising curing the composition according to the invention. Such method may also be carried out in a non-medical setting.

The invention further relates to a cured material, obtainable by the method for preparing a cured material according to the invention.

The kit of parts or curable polymer composition according to the invention may be used for various purposes.

In particular the kit of parts or curable polymer composition is useful in the treatment of a subject having a vascular disease.

In an advantageous embodiment, the treatment of the vascular disease involves the treatment of a human or another mammal, wherein in situ an implant of the cured silicone polymer material is formed, using the kit of parts or curable polymer composition of the invention.

In an advantageous embodiment a use in accordance with the invention comprises the treatment of an aortic aneurysm, preferably an abdominal aortic aneurysm, a thoracic aortic aneurysm or an aneurysm in an iliac artery. In a specific embodiment, the treatment comprises a repair of an endoleak, in particular a type II or a type I endoleak. It is also possible to use the kit of parts or curable polymer composition according to the invention in the treatment of an aneurysm, wherein the composition is for use as an adjuvant filling of the aneurysm in a method wherein an endo-graft is placed in the aneurysm.

Besides treatment of a vascular disease, a kit of parts or curable polymer composition according to the invention is also particularly suitable for use in other prophylactic treatments.

EXAMPLES

Rheology

The samples all have been measured using protocols developed on the Haake VTiQ-Air rheometer equipped with Peltier temperature control. The samples have been tested with a gap of 0.100 mm and 35 mm 2° cone and plate at 37° C.

The viscosity was determined with a 25 s pre-shear at 1 $s^{-1}$ followed by 5 s of low shear rate of 1 $s^{-1}$ and by 5 s of high shear 600 $s^{-1}$. This protocol was followed by 60 s of low shear rate of 1 $s^{-1}$ for the recovery measurement.

For the curing time the protocol used was constant oscillating at 1 Hz and 0.1833 rad for 2400 s.

Mechanical Testing

The mechanical properties of Young's modulus, tensile stress and strain were determined using a Zwick Tensile machine type Z020 equipped with a 1 kN force cell. The samples were cut using a iso 527 type 5A die. The samples were pre-stretched to 0.1 N force with a rate of 5 mm/min. Then the sample was stretched at a rate of 50 mm/min until break.

The hardness was measured using the durometer shore A hardness scale.

Samples are made by weighing the appropriate amount of silica and adding components A1, A2 and A3 or B1, B2 and B3 to the silica ($FS_A$ or $FS_B$) to make a mixture. The mixture is homogenized using Polytron PT 10-35 GT at 8000 RPM for 1 minute. Then the remaining components (catalyst, radio pacifier e.g.) are added and stirred for several minutes using IKA Eurostar 100 at 500 RPM.

Components A and B are mixed using a Medmix MB 4.2-12-LLM/D static mixer and casted into an acrylic mold of 100×100×4 mm (l×b×d). This plate was used for the shore A hardness testing and other mechanical testing.

Table 1 shows the effect of the addition of a hydrophobic fumed silica to a PDMS having different viscosities.

TABLE 1 viscosity of different types of PDMS, with and without 20 wt % R8200

| | | Base PDMS | | | with R8200 | | | Recovery |
|---|---|---|---|---|---|---|---|---|
| | PDMS base wt % | kDa (Mn) | cSt | HS_viscosity @ 600 $s^{-1}$ Pas | LS_viscosity @ 1 $s^{-1}$ Pas | HS_Viscosity @ 600 $s^{-1}$ Pas | LS_Viscosity @ 1 $s^{-1}$ Pas | R8200 wt % | to viscosity to >10 Pas s |
| 1.1 | 80% | 6.0 | 100 | 0.08 | 0.4 | 0.38 | 7.4 | 20% | >60.0 |
| 1.2 | 75% | 6.0 | 100 | 0.08 | 0.4 | 0.73 | 16.1 | 25% | 23.0 |
| 1.3 | 80% | 17.2 | 500 | 0.41 | 0.8 | 1.63 | 32.2 | 20% | 32.0 |
| 1.4 | 85% | 28.0 | 1000 | 0.88 | 1.1 | 2.48 | 5.3 | 15% | >60.0 |
| 1.5 | 82% | 28.0 | 1000 | 0.88 | 1.1 | 3.23 | 10.3 | 18% | >60.0 |
| 1.6 | 80% | 28.0 | 1000 | 0.88 | 1.1 | 4.41 | 45.4 | 20% | 4.0 |
| 1.7 | 80% | 49.5 | 5000 | 3.95 | 4.8 | 7.35 | 55.4 | 20% | <0.5 |
| 1.8 | 80% | 62.7 | 10000 | 5.35 | 8.3 | 11.55 | 70.6 | 20% | <0.5 |
| 1.9 | 80% | 62.7 + vinyl Q | 4500-7000 | 4.30 | 5.2 | 10.89 | 94.0 | 20% | <0.5 |

Table 2 shows the effect of blending a low molecular weight PDMS with a high molecular weight PDMS in the presence of a hydrophobic fumed silica.

TABLE 2

Viscosity measurements of blends of PDMS chains with 20 wt % R8200

| | Base PDMS | | Secondary longer PDMS | | Base PDMS: total PDMS | R8200 | Viscosity @ 600 $s^{-1}$ | Viscosity @ 1 $s^{-1}$ | Recovery to >10 Pas |
|---|---|---|---|---|---|---|---|---|---|
| | wt % | kDa | wt % | kDa | wt % | wt % | Pas | Pas | s |
| 2.1 | 75% | 6.0 | 5% | 49.5 | 93.8 | 20% | 0.64 | 25.3 | >60 |
| 2.2 | 70% | 6.0 | 10% | 49.5 | 87.5 | 20% | 0.66 | 12.1 | >60 |
| 2.3 | 70% | 17.2 | 10% | 49.5 | 87.5 | 20% | 1.73 | 30.0 | 7.5 |
| 2.4 | 65% | 17.2 | 15% | 49.5 | 81.3 | 20% | 2.02 | 47.8 | 9.0 |
| 2.5 | 55% | 17.2 | 25% | 49.5 | 68.8 | 20% | 2.51 | 48.4 | 3.0 |
| 2.6 | 70% | 28.0 | 10% | 49.5 | 87.5 | 20% | 3.21 | 17.7 | >60 |

TABLE 2-continued

Viscosity measurements of blends of PDMS chains with 20 wt % R8200

| Base PDMS | | Secondary longer PDMS | | Base PDMS: total PDMS | R8200 | Viscosity @ 600 s$^{-1}$ | Viscosity @ 1 s$^{-1}$ | Recovery to >10 Pas |
|---|---|---|---|---|---|---|---|---|
| wt % | kDa | wt % | kDa | wt % | wt % | Pas | Pas | s |
| 2.7  | 60% | 6.0  | 20% | 62.7 + vinyl Q | 75.0 | 20% | 1.13 | 24.3 | 53.0 |
| 2.8  | 60% | 6.0  | 20% | 62.7 + vinyl Q | 75.0 | 20% | 1.08 | 26.1 | 51.0 |
| 2.9  | 55% | 17.2 | 25% | 62.7 + vinyl Q | 68.8 | 20% | 2.51 | 50.9 | 4.5 |
| 2.10 | 63% | 6.0  | 17% | 62.7 | 78.8 | 20% | 1.2  | 30.9 | 21.5 |
| 2.11 | 55% | 17.2 | 25% | 62.7 | 68.8 | 20% | 2.84 | 45.9 | 3.0 |

Table 3 shows the effect of addition of different types of fumed silica on the thickening effect of a PDMS base material, and the effect on the recovery of the viscosity in time,

TABLE 3

Examples with a variation in type and concentration of fumed silica

| | PDMS Base | | wt % silica | | Viscosity @ 600 s$^{-1}$ | Viscosity @ 1 s$^{-1}$ | Recovery to >10 Pas |
|---|---|---|---|---|---|---|---|
| | wt % | kDa | wt % | Silica type | Pas | Pas | |
| CE 3.1  | 75% | 6.0  | 25%    | RY50          | 0.21 | 2.00   | >60 |
| CE 3.2  | 85% | 6.0  | 15%    | OX50          | sediments quickly | | |
| 3.3     | 75% | 6.0  | 25%    | R8200         | 0.73 | 16.10  | 10.5 |
| 3.4     | 94% | 6.0  | 6%     | 200           | 0.78 | 289.40 | <0.5 |
| 3.5     | 96% | 6.0  | 4%     | 200           | 0.31 | 37.50  | 2.0 |
| CE 3.6  | 98% | 6.0  | 2%     | 200           | 0.10 | 0.48   | >60 |
| CE 3.7  | 80% | 17.2 | 20%    | R8200         | 3.00 | 21.81  | <0.5 |
| CE 3.8  | 85% | 17.2 | 15%    | R8200         | 1.62 | 6.74   | 32.0 |
| 3.9     | 73% | 17.2 | 27%    | RY50          | 1.62 | 26.86  | <0.5 |
| 3.10    | 78% | 17.2 | 22%    | RY50          | 1.20 | 15.02  | 2.0 |
| CE 3.11 | 84% | 17.2 | 16%    | RY50          | 0.73 | 4.74   | >60 |
| CE 3.12 | 91% | 17.2 | 9%     | R972          | 2.87 | 211.50 | <0.5 |
| 3.13    | 93% | 17.2 | 7%     | R972          | 1.97 | 33.33  | 1.5 |
| 3.14    | 95% | 17.2 | 5%     | R972          | 1.14 | 12.44  | 10.5 |
| CE 3.15 | 97% | 17.2 | 3%     | R972          | 0.72 | 5.33   | >60 |
| 3.16    | 81% | 17.2 | 13%/6% | RY50/R8200    | 1.04 | 14.96  | 9.5 |
| CE 3.17 | 85% | 17.2 | 13%/2% | RY50/R972     | 1.01 | 10.19  | >60 |
| 3.18    | 81% | 17.2 | 7%/12% | RY50/R8200    | 1.08 | 15.83  | 13.0 |
| CE 3.19 | 90% | 17.2 | 7%/3%  | RY50/R972     | 1.12 | 10.76  | >60 |
| CE 3.20 | 85% | 17.2 | 7%/2%/6% | RY50/R972/R8200 | 1.01 | 10.30 | >60 |
| 3.21    | 86% | 17.2 | 2%/12% | R972/R8200    | 1.03 | 11.01  | 59.5 |
| CE 3.22 | 81% | 17.2 | 3%/6%  | R972/R8200    | 1.04 | 9.33   | >60 |

Table 4 shows rheologic properties of cured compositions having a low molecular weight PDMS, optionally a higher molecular weight PDMS, HMS301 as crosslinker and R8200 as fumed silica.

| PDMS Base, vinyl | | Secondary longer PDMS | | HMS-301, | | R8200 | | | |
|---|---|---|---|---|---|---|---|---|---|
| wt % | kDa | wt % | kDa | wt % | [H]:[V] | wt % | LS | HS | rec |
| 4.1 | 59% | 6.0  |     |      | 26% | 5.2  | 15% | 20.5 | 0.5  | >60 |
| 4.2 | 49% | 6.0  | 13% | 62.7 | 22% | 5.2  | 16% | 30.9 | 1.27 | 21.5 |
| 4.3 | 17% | 6.0  | 51% | 17.2 | 15% | 5.2  | 17% | 20.1 | 1.11 | 17 |
| 4.4 | 71% | 17.2 |     |      | 11% | 5.3  | 18% | 26.8 | 1.45 | 9.5 |
| 4.5 | 77% | 49.5 |     |      | 4%  | 5.2  | 19% | 42.4 | 7.45 | <0.5 |
| 4.6 | 45% | 6.0  | 15% | Vinyl Q | 25% | 5.3 | 15% | | | |
| 4.7 | 75% | 6.0  |     |      | 5%  | 0.8  | 20% | 9.5  | 0.4  | >60 |
| 4.8 | 50% | 17.2 |     |      | 31% | 21.1 | 19% | 21.2 | 1.4  | 9.5 |

Table 5 A and B show the effect of a low molecular weight PDMS base material, different amounts of HMS-301 or HMS082 crosslinker, R8200 fumed silica and its effect on viscosity, shear thinning and its rheologic properties after cure.

TABLE 5A

Effect of type and concentration of crosslinker (uncured)

| | PDMS Base | | Crosslinker | | | R8200 | HS_Viscosity | LS_Viscosity | Recovery to 10 Pas |
|---|---|---|---|---|---|---|---|---|---|
| | wt % | kDa | wt % | type | [H:V] | wt % | Pas | Pas | s |
| CE 5.1 | 78% | 6.0 | 3% | HMS-301 | 0.4 | 20% | 0.5 | 15.2 | >60 |
| 5.2 | 75% | 6.0 | 5% | HMS-301 | 0.8 | 20% | 0.5 | 19.3 | >60 |
| 5.3 | 74% | 6.0 | 6% | HMS-301 | 1.0 | 20% | 0.5 | 18.8 | 51 |
| 5.4 | 73% | 6.0 | 7% | HMS-301 | 1.2 | 20% | 0.5 | 17.9 | >60 |
| 5.5 | 71% | 6.0 | 9% | HMS-301 | 1.5 | 20% | 0.7 | 19.5 | 34 |
| 5.6 | 69% | 6.0 | 11% | HMS-301 | 2.0 | 20% | 0.4 | 22.0 | 16 |
| CE 5.7 | 71% | 6.0 | 9% | HMS-082 | 0.4 | 20% | 0.5 | 13.1 | >60 |
| CE 5.8 | 61% | 6.0 | 19% | HMS-082 | 1.0 | 20% | 0.4 | 6.5 | >60 |
| CE 5.9 | 58% | 6.0 | 22% | HMS-082 | 1.2 | 20% | 0.5 | 8.5 | >60 |
| CE 5.10 | 54% | 6.0 | 26% | HMS-082 | 1.5 | 20% | 0.5 | 7.6 | >60 |

TABLE 5B

Effect of type and concentration of crosslinker (cured)

| | PDMS Base | | Crosslinker | | | Young's modulus | Tensile stress | Tensile strain | Hardness | CHCl3 |
|---|---|---|---|---|---|---|---|---|---|---|
| | wt % | kDa | wt % | type | [H:V] | kPa | kPa | % | Shore A | wt % |
| CE 5.1 | 78% | 6.0 | 3% | HMS-301 | 0.4 | No solid cured product | | | | |
| 5.2 | 75% | 6.0 | 5% | HMS-301 | 0.8 | 617.2 | 157.7 | 37.2 | 16.1 | 800.9 |
| 5.3 | 74% | 6.0 | 6% | HMS-301 | 1.0 | 1419.7 | 364.5 | 36.8 | 28.9 | 738 |
| 5.4 | 73% | 6.0 | 7% | HMS-301 | 1.2 | 3067.1 | 526.2 | 25.7 | 47.6 | 513.5 |
| 5.5 | 71% | 6.0 | 9% | HMS-301 | 1.5 | 4577.3 | 515.8 | 14.4 | 55.5 | 549 |
| 5.6 | 69% | 6.0 | 11% | HMS-301 | 2.0 | 3927.9 | 600.0 | 21.0 | 51.8 | 471.3 |
| CE 5.7 | 71% | 6.0 | 9% | HMS-082 | 0.4 | No solid cured product | | | | |
| 5.8 | 61% | 6.0 | 19% | HMS-082 | 1.0 | 310.7 | 226.2 | 105.9 | 5.2 | 387.4 |
| 5.9 | 58% | 6.0 | 22% | HMS-082 | 1.2 | 842.1 | 398.6 | 81.5 | 18.6 | 314.5 |
| 5.10 | 54% | 6.0 | 26% | HMS-082 | 1.5 | 1932.3 | 547.4 | 52.0 | 33.3 | 324.7 |

TABLE 6 blends of hydride or vinyl terminated PDMS chains

| | PDMS vinyl wt % | PDMS vinyl kDa | PDMS hydride wt % | PDMS hydride kDa | Ratio [H]$_p$:[V] | HMS-301 wt % | Ratio [H]$_c$:[V] | R8200 wt % | Young's modulus kPa | Tensile stress kPa | Tensile strain % | Hardness Shore A | CHCl$_3$ absorbed wt % |
|---|---|---|---|---|---|---|---|---|---|---|---|---|---|
| 6.1 | 48% | 6.0 | 24% | 6.0 | 0.5 | 11% | 2.6 | 18% | 880.3 | 497.7 | 71.9 | 29.8 | 632 |
| 6.2 | 45% | 6.0 | 30% | 6.0 | 0.7 | 7% | 1.7 | 19% | 1044.2 | 439.2 | 55.8 | 32.5 | 456 |
| 6.3 | 49% | 17.2 | 23% | 6.0 | 1.4 | 1% | 7.7 | 17% | 593.2 | 429.5 | 111.3 | 19.7 | 628 |
| 6.4 | 35% | 17.2 | 35% | 17.2 | 1.0 | 11% | 10.7 | 18% | 92.9 | 175.7 | 138.7 | 10.7 | 690 |
| 6.5 | 45% | 17.2 | 32% | 17.2 | 0.7 | 4% | 2.6 | 19% | 634.1 | 857.8 | 206.5 | 20.4 | 656 |
| 6.6 | 49% | 17.2 | 30% | 17.2 | 0.6 | 2% | 1.4 | 19% | 539.7 | 565.8 | 154.2 | 18.1 | 612 |
| 6.7 | 47% | 17.2 | 19% | 17.2 | 0.4 | 14% | 10.5 | 20% | 609.3 | 720.8 | 168.3 | 20.6 | 561 |
| 6.8 | 40% | 6.0 | 39% | 17.2 | 1.0 | 2% | 0.7 | 19% | 261.3 | 338.8 | 164.4 | 3.0 | 873 |
| 6.9 | 77% | 49.5 | | | | 4% | 5.2 | 19% | 1339.7 | 1346.5 | 212.7 | 26.4 | 539 |

Table 6 shows the effect of curing kit of parts having different components A and B, different ratios and fumed silica on physical properties.

Table 7 shows compositions of different kits of parts. Rheologic properties of the A and B parts are disclosed in table 8 (before curing).

Table 9 shows the results of the same compositions, after steam sterilisation, and the properties after curing.

TABLE 7

Formulation of blends with radio pacifier

| | PDMS vinyl, 6.0 kDa wt % | PDMS vinyl, 17.2 kDa wt % | PDMS hydride, 6.0 kDa wt % | PDMS hydride, 17.2 kDa wt % | Ratio $[H]_p$:$[V]$ | HMS-301 wt % | Ratio $[H]_c$:$[V]$ | R8200 wt % | 200 wt % | Ta wt % |
|---|---|---|---|---|---|---|---|---|---|---|
| 7.1 | 30% | | | 30% | 0.3 | 2% | 0.7 | 19% | | 20% |
| 7.2 | 12% | 18% | | 30% | 0.6 | 1% | 0.7 | 19% | | 20% |
| 7.3 | 3% | 27% | | 30% | 0.8 | 1% | 0.7 | 19% | | 20% |
| 7.4 | 24% | | 17% | 7% | 0.8 | 1% | 0.7 | 21% | | 30% |
| 7.5 | 25% | | 19% | 6% | 0.8 | 1% | 0.7 | 18% | 1% | 30% |
| 7.6 | 26% | | 19% | 6% | 0.8 | 2% | 0.7 | 16% | 1% | 30% |

TABLE 8 results of viscosity measurements of not sterilized blends with tantalum

| Virgin CE | Part A HS_viscosity Pas | LS_viscosity Pas | Recovery @ 0.5 s Pas | Recovery to 5 Pas s | Recovery to 10 Pas s | Recovery to 20 Pas s | Part B HS_viscosity Pas | LS_viscosity Pas | Recovery @ 0.5 s Pas | Recovery to 5 Pas s | Recovery to 10 Pas s | Recovery to 20 Pas s |
|---|---|---|---|---|---|---|---|---|---|---|---|---|
| 7.1 | 0.88 | 24.9 | 1.4 | 4.0 | 9.5 | >60 | 2.28 | 56.0 | 0.2 | 3.5 | 7.0 | 40.0 |
| 7.2 | 1.64 | 32.1 | 3.2 | 3.0 | 8.0 | 45.5 | 1.88 | 28.7 | 4.4 | 1.0 | 17.0 | >60 |
| 7.3 | 0.89 | 37.3 | 3.4 | 2.5 | 7.0 | >60 | 1.81 | 27.6 | 3.9 | 3.5 | 18.5 | >60 |
| 7.4 | 1.64 | 112.0 | 6.5 | 0.5 | 1.5 | 3.0 | 1.42 | 61.8 | 1.3 | 2.0 | 2.5 | 5.5 |
| 7.5 | 1.36 | 71.8 | 3.3 | 1.5 | 2.5 | 6.0 | 1.08 | 41.3 | 4.8 | 1.0 | 4.0 | 16.5 |
| 7.6 | 1.09 | 44.7 | 5.8 | 0.5 | 3.0 | 10.5 | 0.93 | 36.0 | 0.4 | 2.5 | 5.0 | 36.0 |

| Steam | Part A HS_viscosity Pas | LS_viscosity Pas | Recovery @ 0.5 s Pas | Recovery to 5 Pas s | Recovery to 10 Pas s | Recovery to 20 Pas s | Part B HS_viscosity Pas | LS_viscosity Pas | Recovery @ 0.5 s Pas | Recovery to 5 Pas s | Recovery to 10 Pas s | Recovery to 20 Pas s |
|---|---|---|---|---|---|---|---|---|---|---|---|---|
| 7.1 | | | | | | | | | | | | |
| 7.2 | | | | | | | | | | | | |
| 7.3 | 2.2 | 104 | 7.3 | 0.5 | 1.0 | 2.0 | 2.01 | 78.3 | 6.9 | 0.5 | 1.0 | 2.5 |
| 7.4 | 1.8 | 210 | 16.7 | 0.5 | 0.5 | 1.0 | 1.86 | 228 | 9.6 | 0.5 | 1.0 | 1.5 |
| 7.5 | 1.35 | 132 | 23.2 | 0.5 | 0.5 | 0.5 | 0.83 | 51.6 | 3.3 | 1.0 | 2.0 | 3.5 |
| 7.6 | 1.32 | 150 | 12.5 | 0.5 | 0.5 | 1.0 | 1.09 | 81.0 | 8.5 | 0.5 | 1.0 | 2.0 |

| Steam | Young's modulus kPa | Tensile stress kPa | Tensile strain % | Hardness Shore A | CHCl3 absorbed wt % |
|---|---|---|---|---|---|
| 7.1 | 436.7 | 557.9 | 159.2 | 17.9 | 639 |
| 7.2 | 686.5 | 963.1 | 233.7 | 23.4 | 603.2 |
| 7.3 | 807.3 | 1328.9 | 363.5 | 23.3 | 660.2 |
| 7.4 | 1004.2 | 1543.1 | 218.8 | 30.1 | 391.7 |
| 7.5 | 659.7 | 999.3 | 179.4 | 23.2 | 463.2 |
| 7.6 | 764.7 | 940.4 | 160.1 | 24.9 | 454.7 |

Table 10 different Karstedt and 2,4,6,8-Tetramethyl-2,4, 6,8-tetravinylcyclotetrasiloxane (MVCS) ratios, shown with the curing time

|  | | Virgin | | Steam sterilized | | |
| --- | --- | --- | --- | --- | --- | --- |
|  | Karstedt concentration | crossover point (delta 45°) | Cured (delta 10°) | crossover point (delta 45°) | Cured (delta 10°) | ratio (kar/ MVCS) |
| 8.1 | ppm | s | s | s | s | wt/wt |
| 8.2 | 0.3 | 164 | 296 | 1960 | >2400 | No inhibitor |
| 8.3 | 72.2 | 232 | 284 | 228 | 280 | 0.25 |
| 8.4 | 233.0 | 356 | 480 | 360 | 480 | 0.27 |
| 8.5 | 463.4 | 88 | 120 | 164 | 284 | 0.54 |
| 8.6 | 660.0 | 44 | 60 | 144 | 172 | 0.77 |

Experiments have been repeated from EP1435249 (Vesalius) to show that these experiments do not provide compositions having a high viscosity at low shear, and a fast recovery after shear. The experiments have been summarized in table 11 below.

TABLE 11

Experiments from EP1435249 (Vesalius)

| | Composition | | | | | | Viscosity measurements | | | | | |
| --- | --- | --- | --- | --- | --- | --- | --- | --- | --- | --- | --- | --- |
| | Base | | | | | | Part A | | | Part B | | |
| | | PDMS 28.0 kDa | | for part A | | for part B | HS_Viscosity @ 600 | LS_viscosity @ 1 | recovery to viscosity | HS_Viscosity @ 600 | LS_viscosity @ 1 | Recovery to viscosity |
| | VinylQ wt % | 1000 cSt wt % | R8200 wt % | HMS-301 wt % | Base wt % | Cat wt % | Base wt % | s-1 Pas | s-1 Pas | of >5 Pas s | s-1 Pas | s-1 Pas | of >5 Pas s |
| vesalius example 2 | 20.0% | 70.0% | 10.0% | 20% | 80% | 0.7% | 99.3% | 0.94 | 3.09 | >60 | 2.05 | 5.74 | >60 |
| vesalius example 3 | 30.0% | 67.0% | 3.0% | 23% | 77% | 0.7% | 99.3% | 0.71 | 2.32 | >60 | 1.57 | 3.46 | >60 |
| vesalius example 4 | 35.5% | 59.5% | 5.0% | 20% | 80% | 0.7% | 99.3% | 0.94 | 2.75 | >60 | 2.02 | 4.25 | >60 |
| vesalius example 5 | 49.0% | 49.9% | 1.1% | 37% | 63% | 1.4% | 98.6% | 0.51 | 2.04 | >60 | 1.99 | 3.17 | >60 |

What is claimed is:

1. A kit of parts suitable for preparing a cured biocompatible silicone polymer material, the kit comprising:
at least 2 containers each containing a fluid component, which components—when mixed—form a fluid curable biocompatible polymer composition, which upon curing forms the cured biocompatible silicone polymer material, wherein a first container comprises a fluid component A, which component A comprises
  a. a divinyl substituted polydimethylsiloxane A1 (PDMS A1) having a viscosity between 50 and 600 cSt at 25° C.,
  b. optionally a divinyl substituted polydimethylsiloxane A2 (PDMS A2) having a viscosity between 1000 and 20000 cSt at 25° C.,
  c. a Pt catalyst soluble in polydimethylsiloxane (PDMS)
  d. a hydrophobic fumed silica $FS_A$ having been partially surface treated
  e. optionally a crosslinker A3 having more than 2 vinyl groups per molecule
and wherein a second container comprises a fluid component B, which component B comprises,
  f. a dihydride substituted polydimethylsiloxane B1 (PDMS B1) having a viscosity between 50 and 600 cSt,
  g. optionally a dihydride substituted polydimethylsiloxane B2 (PDMS B2) having a viscosity between 1000 and 20000 cSt at 25° C.,
  h. a hydrophobic fumed silica $FS_B$ having been partially surface treated
  i. a crosslinker B3 having more than 2 hydrosilyl groups,
wherein the amount of the polydimethylsiloxane A1 is at least 70 wt % relative to the total of the PDMS A1 and the PDMS A2,
wherein the amount of the PDMS B1 is at least 70 wt % relative to the total of the PDMS B1 and the PDMS B2,
wherein the amount of the crosslinker A3 ranges between 0 and 10 wt % relative to the weight of the component A,
wherein the amount of the $FS_A$ and the $FS_B$ ranges between 2 and 30 wt % relative to the total weight of the component A+the component B,
wherein a volume to volume ratio of the component AZ:the component B is in the range of 1:3 to 3:1,
wherein the components A and B are both fluids, having a viscosity between 10 and 200 Pa·s at a shear rate of 1 s$^{-1}$, and a viscosity below 2 Pa·s at a shear rate of 600 s$^{-1}$ and wherein the components A and B when mixed form a composition having a viscosity of at least 10 Pa·s when sheared at 1 s$^{-1}$, and a viscosity below 2.0 Pa·s when sheared at 600 s$^{-1}$,
and wherein the viscosity of the composition recovers to a value of at least 10 Pa·s when high shearing is stopped with a recovery time of less than 60 sec, wherein the viscosity is determined according to with a Haake VTiQAir rheometer at 37° C.

2. The kit of parts according to claim 1, wherein in the PDMS A1 one vinyl group is attached to each terminal of the polymer molecule, such that the polymer molecule starts with a first vinyl group, the main chain of the polymer is a linear PDMS and the polymer molecule ends with a second vinyl group, and wherein the crosslinker A3 is chosen from a functionalised molecular silica compound and 1,3,5,7-tetravinyl-1,3,5,7-tetramethylcyclotetrasiloxane.

3. The kit of parts according to claim 1, wherein the fumed silica $FS_A$ and the fumed silica $FS_B$ have a number average particle size typically ranging between 10 and 100 nm, and their surfaces are partially treated with an organic agent to provide organic groups attached to the surface of the fumed silica, wherein the fumed silica $FS_A$ and the fumed silica $FS_B$ have 0.5-5 wt % carbon, which partly covers the surface of the fumed silica, and wherein the amount of the fumed silica $FS_A$ ranges between 2 and 30 wt % relative to the component A, and wherein the amount of the fumed silica $FS_B$ ranges between 2 and 30 wt % relative to the total weight of the component B.

4. The kit of parts according to claim 1, wherein the component A and/or the component B also comprise between 0.1 and 5 wt % of a hydrophilic fumed silica.

5. The kit of parts according to claim 1, wherein the PDMS A1 is a blend with a first PDMS A1-1 having a viscosity of 100 cSt blended with a second PDMS A1-2 having a viscosity of 500 cSt at 25° C.

6. The kit of parts according to claim 1, wherein the PDMS B1 is a blend with a first PDMS B1-1 having a viscosity of 100 cSt blended with a second PDMS B1-2 having a viscosity of 500 cSt at 25° C.

7. The kit of parts according to claim 1, wherein in the PDMS B1 and the PDMS B2 the two hydrosilyl groups are attached to each terminal of the PDMS chains, and
   wherein the PDMS B1 is a dihydride substituted polydimethylsiloxane B1 having a viscosity between 50 and 600 cSt at 25° C. or wherein the PDMS B1 has a viscosity between 0.3 and 1 Pa·s when sheared at 1 $s^{-1}$.

8. The kit of parts according to claim 1, wherein the PDMS A1 is a divinyl substituted polydimethylsiloxane A1 having a viscosity between 50 and 600 cSt at 25° C. or wherein the PDMS A1 has a viscosity between 0.3 and 1 Pa·s when sheared at 1 $s^{-1}$.

9. The kit of parts according to claim 1, wherein the crosslinking agent B3 is a polymethylhydrosilane.

10. The kit of parts according to claim 1, wherein a molar ratio of all vinyl groups from the PDMS A1+the PDMS A2 and the optional crosslinker A3 of the component A to all hydrosilyl groups from the PDMS B1+the PDMS B2+the crosslinker B3 range between 1:1 and 1:6.

11. The kit of parts according to claim 1, wherein a total amount of the PDMS A1+the PDMS A2, the fumed silica $FS_A$ and the crosslinker A3 is at least 50 wt % of the component A and wherein a total amount of the PDMS B1+the PDMS B2, the fumed silica $FS_B$ and the crosslinker B3 is at least 50 wt % of component B.

12. The kit of parts according to claim 1, wherein at least the PDMS A2 or the PDMS B2 is present.

13. The kit of parts according to claim 1, wherein an amount of the PDMS A2+the PDMS B2 is between 10 and 30 wt % relative to an amount of the PDMS A1+the PDMS A2+the PDMS B1+the PDMS B2.

14. A curable silicone polymer composition, obtained by mixing the kit of parts as defined in claim 1.

15. The curable silicone polymer composition according to claim 14, wherein the composition has a viscosity of at least 10 Pa·s when sheared at 1 $s^{-1}$, and a viscosity below 2.7 Pa·s when sheared at 600 $s^{-1}$ and wherein the viscosity of the composition recovers to a value of at least 10 Pa·s when high shearing is stopped with a recovery time of less than 60 sec.

16. A cured silicon polymer composition obtained by curing the composition according to claim 15, wherein the cured composition has a Young's modulus of between 0.3 and 3 MPa and a hardness between 10 and 44 ShA.

17. The cured polymer material according to claim 16, wherein the cured polymer has a strain or an elongation at break of between 50 and 600%, and a stress at break of between 100 and 1500 kPa.

18. The kit of parts according to claim 2, wherein the fumed silica $FS_A$ and the fumed silica $FS_B$ have a number average particle size typically ranging between 10 and 100 nm, and their surfaces are partially treated with an organic agent to provide organic groups attached to the surface of the fumed silica, wherein the fumed silica $FS_A$ and the fumed silica $FS_B$ have 0.5-5 wt % carbon, which partly covers the surface of the fumed silica, and wherein the amount of the fumed silica $FS_A$ ranges between 2 and 30 wt % relative to the component A, and wherein the amount of the fumed silica $FS_B$ ranges between 2 and 30 wt % relative to the total weight of the component B,
   wherein the component A and/or the component B also comprise between 0.1 and 5 wt % of a hydrophilic fumed silica, and
   wherein PDMS A1 is a blend with a first PDMS A1-1 having a viscosity of 100 cSt blended with a second PDMS A1-2 having a viscosity of 500 cSt at 25° C.

19. The kit of parts according to claim 18, wherein the PDMS B1 is a blend with a first PDMS B1-1 having a viscosity of 100 cSt blended with a second PDMS B1-2 having a viscosity of 500 cSt at 25° C.,
   wherein in the PDMS B1 and the PDMS B2 the two hydrosilyl groups are attached to each terminal of the PDMS chains, and wherein the PDMS B1 is a dihydride substituted polydimethylsiloxane B1 having a viscosity between 50 and 600 cSt at 25° C. or wherein the PDMS B1 has a viscosity between 0.3 and 1 Pa·s when sheared at 1 $s^{-1}$, and
   wherein the PDMS A1 is a divinyl substituted polydimethylsiloxane A1 having a viscosity between 50 and 600 cSt at 25° C. or wherein the PDMS A1 has a viscosity between 0.3 and 1 Pa·s when sheared at 1 $s^{-1}$.

20. The kit of parts according to claim 19, wherein the crosslinking agent B3 is a polymethylhydrosilane wherein a molar ratio of all vinyl groups from the PDMS A1+the PDMS A2 and the optional crosslinker A3 of the component A to all hydrosilyl groups from the PDMS B1+the PDMS B2+the crosslinker B3 range between 1:1 and 1:6, wherein a total amount of the PDMS A1+the PDMS A2, the fumed silica $FS_A$ and the crosslinker A3 is at least 50 wt % of the component A and wherein a total amount of the PDMS B1+the PDMS B2, the fumed silica $FS_B$ and the crosslinker B3 is at least 50 wt % of component B,
   wherein at least the PDMS A2 or the PDMS B2 is present, and
   wherein an amount of the PDMS A2+the PDMS B2 is between 10 and 30 wt % relative to an amount of the PDMS A1+the PDMS A2+the PDMS B1+the PDMS B2.

\* \* \* \* \*